(12) United States Patent
Han et al.

(10) Patent No.: US 12,016,690 B2
(45) Date of Patent: Jun. 25, 2024

(54) CHARACTERIZATION OF INJECTION-INDUCED TISSUE SWELLING DURING SUBCUTANEOUS INJECTION OF BIOLOGICS

(71) Applicant: Purdue Research Foundation, West Lafayette, IN (US)

(72) Inventors: Bumsoo Han, West Lafayette, IN (US); Yingnan Shen, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 896 days.

(21) Appl. No.: 16/779,695

(22) Filed: Feb. 3, 2020

(65) Prior Publication Data

US 2020/0253522 A1 Aug. 13, 2020

Related U.S. Application Data

(60) Provisional application No. 62/804,637, filed on Feb. 12, 2019.

(51) Int. Cl.
*G06T 7/00* (2017.01)
*A61B 5/00* (2006.01)
(Continued)

(52) U.S. Cl.
CPC ...... *A61B 5/150106* (2013.01); *A61B 5/0033* (2013.01); *A61B 5/0064* (2013.01);
(Continued)

(58) Field of Classification Search
CPC ............ A61B 5/150106; A61B 5/0033; A61B 5/0064; A61B 5/0077; A61B 5/150167; A61B 5/0071; A61L 27/3804; C12M 33/04; C12M 41/46; G01N 21/00; G01N 21/6456; G01N 33/4833; G06T 7/0012; G06T 2207/10064; G06T 2207/30088; G09B 23/306; C12N 5/0656

See application file for complete search history.

(56) References Cited

U.S. PATENT DOCUMENTS 9,310,302 B2 * 4/2016 Garsha ............... G01N 21/6456
2013/0027539 A1 * 1/2013 Kiyota .................... C12M 41/36
348/79
2017/0138926 A1 * 5/2017 Chubykin ........ G01N 33/48728

FOREIGN PATENT DOCUMENTS

WO WO-2017039043 A1 * 3/2017 ............ B01L 3/5027
WO WO-2018026172 A1 * 2/2018 ........... B29C 64/106

OTHER PUBLICATIONS

Gholobova et al., "Human tissue-engineered skeletal muscle: a novel 3D in vitro model for drug disposition and toxicity after intramuscular injection", Aug. 2018, Scientific Reports, 8:12206 (Year: 2018).*

(Continued)

*Primary Examiner* — Samuel P Siefke
*Assistant Examiner* — Henry H Nguyen
(74) *Attorney, Agent, or Firm* — Flaster Greenberg P.C.

(57) ABSTRACT

Disclosed herein is a platform and method to quantify spatiotemporal tissue swelling during biologics injection, and to predict associated increase in the mechanical stress and interstitial fluid pressure (IFP) of tissues. Accurate measure and estimation of tissue swelling, thus, can be quantitative and predictive indicator of the IPD.

10 Claims, 4 Drawing Sheets

(51) Int. Cl.
  *A61B 5/15* (2006.01)
  *A61L 27/38* (2006.01)
  *C12M 1/26* (2006.01)
  *C12M 1/34* (2006.01)
  *G01N 21/00* (2006.01)
  *G01N 21/64* (2006.01)
  *G01N 33/483* (2006.01)
  *G09B 23/30* (2006.01)

(52) U.S. Cl.
  CPC ...... *A61B 5/0077* (2013.01); *A61B 5/150167* (2013.01); *A61L 27/3804* (2013.01); *C12M 33/04* (2013.01); *C12M 41/46* (2013.01); *G01N 21/00* (2013.01); *G01N 21/6456* (2013.01); *G01N 33/4833* (2013.01); *G06T 7/0012* (2013.01); *G09B 23/306* (2013.01); *G06T 2207/10064* (2013.01); *G06T 2207/30088* (2013.01)

(56) References Cited

OTHER PUBLICATIONS

Koffler et al., "Improved vascular organization enhances functional integration of engineered skeletal muscle grafts", 2011 PNAS, 108 (38), 14789-14794 (Year: 2011).*
Translation of WO2018026172A1, Cho, Dong-Woo, Feb. 8, 2018 (Year: 2018).*
Translation of WO2017039043A1, Jeon, Noo Li, Mar. 9, 2017 (Year: 2017).*
Jones. G. B., et al., Subcutaneous drug delivery: An evolving enterprise. Sci Transl Med. Aug. 30, 2017; 9(405).
Sato. M., et al., FRI0174 Pain assessment for subcutaneous injection of biologics in the treatment of rheumatoid arthritis. Annals of the Rheumatic Diseases 2013;72:A430-A431.
Teo, K. et al., Spatiotemporal measurement of freezing-induced deformation of engineered tissues. Journal of biomechanical engineering, 132(3), 031003.
Teo, K. et al., Effects of freezing-induced cell-fluid-matrix interactions on the cells and extracellular matrix of engineered tissues. Biomaterials, 32(23), 5380-5390.

\* cited by examiner

CHARACTERIZATION OF INJECTION-INDUCED TISSUE SWELLING DURING SUBCUTANEOUS INJECTION OF BIOLOGICS

FIELD OF INVENTION

This application relates to the apparatus to characterize injection-induced pain and discomfort. Particularly, a platform to quantify spatiotemporal tissue swelling during injection of biologics is disclosed herein.

BACKGROUND

Recent emergence in biologics provides effective solutions to treat a variety of diseases that presently have no other treatment options available [1]. These include vaccines, blood and blood components, somatic cells, tissues, and recombinant therapeutic proteins. Biologics can be composed of sugars, proteins, or nucleic acids or complex combinations of these substances, or may be living entities such as cells and tissues. Typical delivery routes of biologics are injection or intravenous infusion. Because of large molecular weight of these biologics, however, effective administration of this type of drugs pose significant challenges. Particularly, pain and discomfort induced during subcutaneous (SQ) injection of biologics pose significant challenges to broader use of biologic drugs, design and development of injection and infusion devices, and quality of patient's life [2]. Thus, it is critically important to be able to assess and quantify the extent of the injection-induced pain and discomfort (IPD). However, current available methods are mostly very subjective and inadequate to quantify the extent of IPD.

SUMMARY OF THE INVENTION

In this study, we develop a new biomimetic platform to quantify spatiotemporal tissue swelling during injection of biologics, and to predict associated increase in mechanical stress and interstitial fluid pressure (IFP) of tissues.

IPD is likely caused by tissue swelling and subsequent increase in mechanical stress and IFP of tissues near injection sites. This mechanical stress and fluid pressure stimulate nociceptors, which are primarily present at the dermis of the skin. Accurate measure and estimation of tissue swelling, thus, can be a quantitative and predictive indicator of the IPD. Thus, we construct and test an experimental setup capable of measuring injection-induce swelling of engineered tissue constructs.

These and other features, aspects and advantages of the present invention will become better understood with reference to the following figures, associated descriptions and claims.

BRIEF DESCRIPTION OF THE DRAWINGS

FIG. 2.

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Methods

Figure 1:
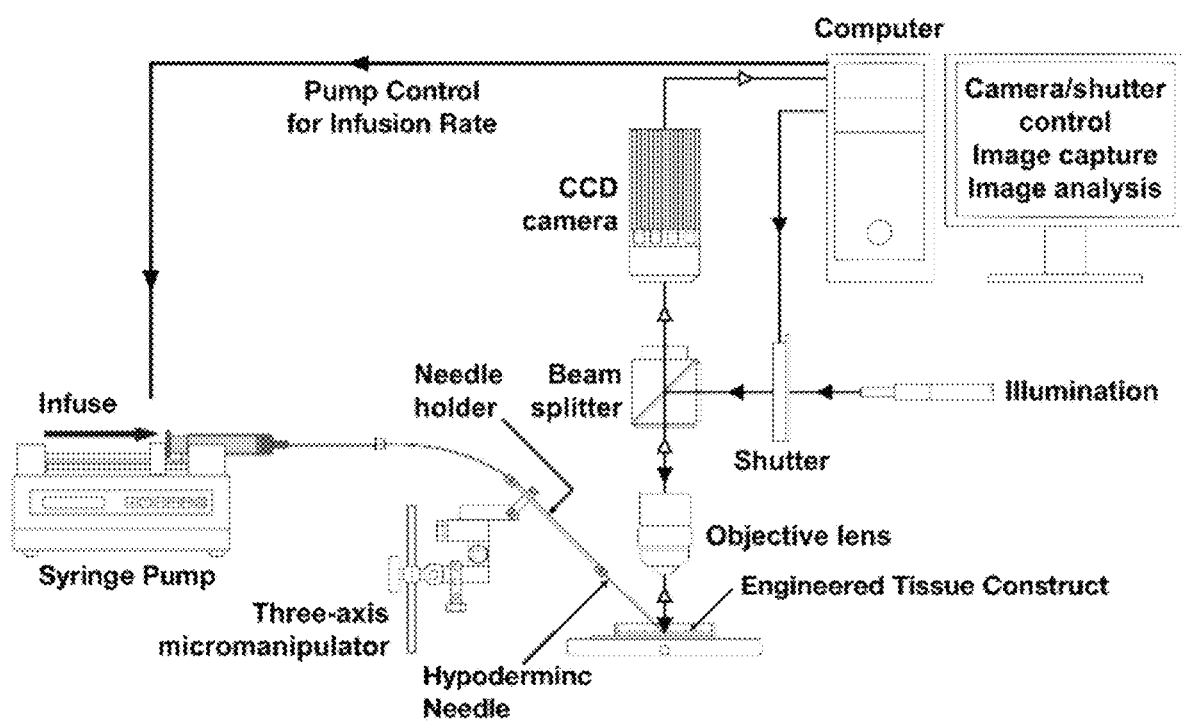
FIG. 1. Schematic of experimental setup.

A schematic of the testing platform is shown in FIG. 1. The platform consists of injection system, imaging system and engineered tissue constructs (ETCs). The injection system infuses or injects biologic drugs and macromolecules into the ETCs at various injection rates to simulate a wide range of injection conditions. The ETCs are prepared by seeding quantum dot (QD)-labeled fibroblasts in collagen matrices whose mechanical and chemical properties are designed to mimic the dermal layer of skin. The imaging system including a fluorescence macro/microscope and a CCD camera images QD-labeled fibroblasts during injection of biologics drugs, and determine the spatiotemporal deformation of ETCs.

The detailed description of the construction of engineered tissues can be found in our prior publications [2, 3]. Briefly, the early human foreskin fibroblasts were cultured up to 17th passage and consistently harvested at 80~90% confluency. The collected cells were labeled with quantum dots by being mixed with the labeling solution and incubated for 45 min. After incubation, the cells were washed twice to remove the excess quantum dots. To construct the engineered tissue mimicking the dermal layer of skin, the labeled fibroblasts were suspended in 1.5 mL of type I collagen solution containing 3 mg/mL collagen, and the cell concentration was $2 \times 10^5$ cells/mL.

Figures 2A, 2B:
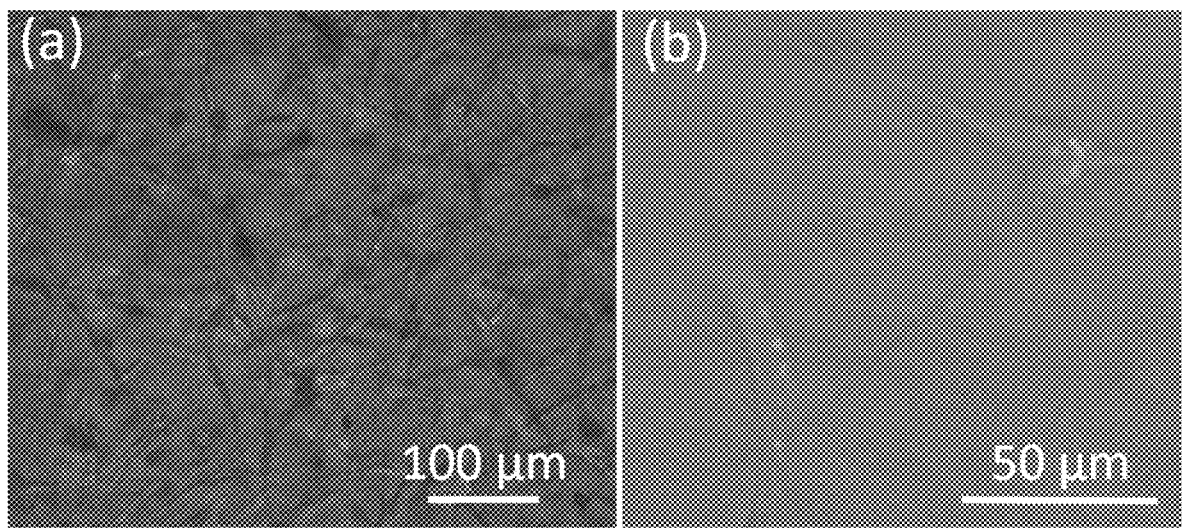
FIG. 2A: (a) Labeled fibroblasts, embedded in collagen matrix.
FIG. 2B: (b) Quantum dots accumulate in the cytoplasm of dendritic fibroblasts.

The collagen solution containing labeled fibroblasts was placed in a cylindrical hole punched through a PDMS layer filling a petri dish. The dimension of the hole is 11 cm$^2$×1 cm. The engineered tissue was generated when the fibroblasts-contained collagen solution polymerized at 37° C. for 1.5 hours. After being incubated with complete culture medium for 24 hours, as shown in FIG. 2, the fibroblasts embedded in collagen matrix developed a dendritic morphology and were still labeled with QDs. FIG. 2B shows that the QDs accumulate in the cytoplasm.

Figures 3A, 3B:
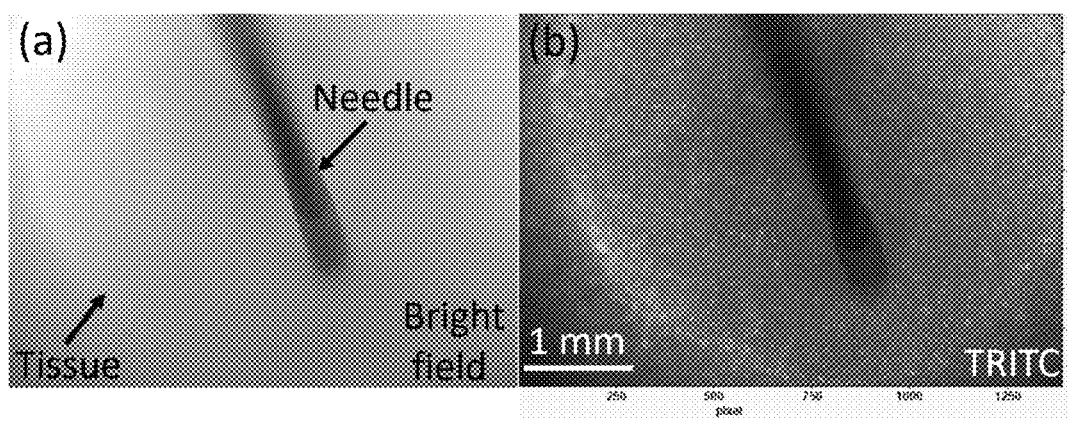
FIG. 3. Brightfield (FIG. 3A) and fluorescence (TRITC filter, FIG. 3B) images of the engineered tissue during the injection.

As shown in FIG. 3A, a conventional 27-gauge needle was manipulated to penetrate into the engineered tissue. The injection rate ranged within 0.3~3 mL/min, which was lower than the subcutaneous injection rate in hospital due to the small size of the tested tissue. During the injection, the tissue was continuously imaged with a 0.2 s interval. As shown in FIG. 3B, the QD-labeled cells were visualized with a TRITC filter, and the fluorescence image showed the entire tissue was labeled by fluorescence particles.

Figure 4:
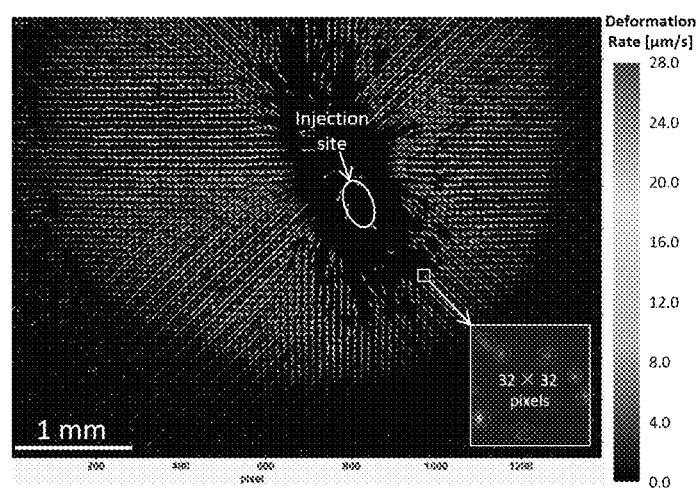
FIG. 4. Deformation rate vector field indicating the tissue swelling during the injection.

The acquired sequential images were cross-correlated to estimate the local deformation rates throughout the tissue during the injection. Briefly, a pair of consecutive images was put into the DaVis software, and each of the images was divided into a grid of 32×32 pixels (1 pixel equals 4 µm) interrogation windows. The density of the fluorescence particle pairs was large enough to guarantee that there were typically more than 4 fluorescence particles in each interrogation window. The interrogation windows in the consecutive images were cross-correlated to generate correlation peaks, the location of which provided the deformation rate vector in the corresponding interrogation window. As shown in FIG. 4, a vector was generated in a 32×32 pixels interrogation window containing 7 fluorescence particles which were used to perform cross-correlation. Multi-pass processing was used with decreasing interrogation window size (2 iterations of 64×64 pixels followed by 3 iterations of 32×32 pixels) and 50% overlap.

Results and Discussion

A representative spatiotemporal deformation rate of the dermal equivalent is shown in FIG. 4. The deformation rate vector field of the tissue was determined in terms of pixel/s. The tissue swelling during the injection is clearly shown by the vector field, and the vectors indicating the largest local deformation rates locate close to the needle injection site. The largest deformation rate is up to 7 pixels/s which equals 28 μm/s, and the deformation rate gradually decreases below 2 pixels/s which equals 8 μm/s when it reaches the outskirt of the tissue. The region without vectors is due to that the needle blocks the view of the tissue, as well as that the deformation of the tissue due to the penetration of the needle causes the area near the injection site to be out of focus.

In the present study, we demonstrated the feasibility of measuring injection-induced deformation, which is expected to cause IPD using dermal equivalents and digital image correlation. Without being limited by any theory, the underlying rationale is that most nociceptors are present at the dermal layer, even though injection occurs at the SQ layer. The mechanical stress and fluid pressure stimulate nociceptors, which are primarily present at the dermis of the skin. However, we plan to further develop the ETCs by adding adipocytes, hyaluronic acids and fibronectins to create more realistic dermal and subcutaneous tissue models. The platform can also measure transport of biologic drugs at various injection conditions. Ultimately the platform will provide a reliable test bed to systematically design and optimize biologic drugs, their injection devices and schemes.

REFERENCES

[1] Jones, G. B., Collins, D. S., Harrison, M. W., Thyagarajapuram, N. R., & Wright, J. M. (2017). Subcutaneous drug delivery: An evolving enterprise. Science translational medicine, 9(405).
[2] Sato, M., Takemura, M., & Shinohe, R. (2013). FRI0174 Pain assessment for subcutaneous injection of biologics in the treatment of rheumatoid arthritis. Annals of the Rheumatic Diseases, 72, A430.
[3] Teo, K. Y., Dutton, J. C., & Han, B. (2010). Spatiotemporal measurement of freezing-induced deformation of engineered tissues. Journal of biomechanical engineering, 132(3), 031003.
[4] Teo, K. Y., DeHoyos, T. O., Dutton, J. C., Grinnell, F., & Han, B. (2011). Effects of freezing-induced cell-fluid-matrix interactions on the cells and extracellular matrix of engineered tissues. Biomaterials, 32(23), 5380-5390.

What is claimed is:

1. A system for measuring a biologics moiety associated injection-induced pain and discomfort (IPD), comprising:
   an engineered tissue construct (ETC) configured to receive a biologics moiety injection, the ETC comprising two or more skin equivalent layers and a labeled tissue present in at least one layer of the two or more skin equivalent layers, wherein the labeled tissue comprises labeled fibroblasts embedded in a collagen matrix;
   an adjustable injection system-configured to provide the biologics moiety at a controlled rate to the labeled tissue; and
   an imaging system for measuring injection induced tissue deformation, wherein the imaging system is configured to obtain two or more consecutive images of an area of the labeled fibroblasts during an injection of the biologics moiety; and
   wherein the imaging system comprises one or more processors and a non-transitory computer readable medium comprising instructions that, when executed by the at least one processor, cause the imaging system to obtain the two or more consecutive images of the area of the labeled fibroblasts during an injection of the biologics moiety and divide the area of the labeled fibroblasts in each of the two or more consecutive images into a grid of interrogation windows, and cross-correlate corresponding interrogation windows of each image to generate a deformation vector at a location of each corresponding interrogation window.

2. The system according to claim 1, wherein the biologics moiety is selected from the group consisting of vaccines, blood or blood components, somatic cells, tissues, recombinant therapeutic proteins, and combinations thereof.

3. The system according to claim 1, wherein the ETC is derived from early human foreskin fibroblasts with minimum passage of about 10 generations.

4. The system according to claim 3, wherein the fibroblasts are labeled with quantum dots.

5. The system according to claim 4, wherein the labeled fibroblasts are suspended in type I collagen solution and molded into the ETC by polymerizing in a defined container.

6. The system according to claim 1, wherein the ETC further comprises adipocytes, hyaluronic acids and/or fibronectins.

7. The system according to claim 1, wherein the adjustable injection system comprises at least one injection needle that is manipulated to penetrate the ETC.

8. The system according to claim 1, wherein the adjustable injection system comprises a syringe pump to control an infusion rate of the biologics moiety to a hypodermic injection needle.

9. The system according to claim 1, wherein the adjustable injection system comprises a three-axis micro-manipulator and a needle holder.

10. The system according to claim 1, wherein the imaging system comprises a microscope and a charge-coupled device camera.

* * * * *